United States Patent [19]

Barth

[11] Patent Number: 4,537,680

[45] Date of Patent: Aug. 27, 1985

[54] INTEGRAL FLUID FILTER AND CAPILLARY

[75] Inventor: Phillip W. Barth, Palo Alto, Calif.

[73] Assignee: The Board of Trustees of the Leland Stanford Junior University, Stanford, Calif.

[21] Appl. No.: 616,658

[22] Filed: Jun. 4, 1984

[51] Int. Cl.³ .............................................. B01D 31/00
[52] U.S. Cl. .................................... 210/316; 210/437; 210/498
[58] Field of Search ............... 210/316, 437, 496, 498, 210/510, 900, 198.2; 55/386

[56] References Cited

U.S. PATENT DOCUMENTS

| | | | |
|---|---|---|---|
| 2,727,632 | 12/1955 | Mack | 210/510.1 |
| 2,752,731 | 7/1956 | Altosaar | 210/510.1 |
| 3,482,703 | 12/1969 | Roberts et al. | 210/510.1 |
| 4,116,836 | 9/1978 | DeAngelis | 55/386 |
| 4,283,210 | 8/1981 | Mochida et al. | 210/510.1 |

Primary Examiner—John Adee
Attorney, Agent, or Firm—Flehr, Hohbach, Test, Albritton & Herbert

[57] ABSTRACT

A comb filter including a first plurality of generally parallel grooves and a capillary including a second groove connected to the first plurality of grooves are integrally formed in a substrate such as by selective etching a surface of a semiconductor substrate. A cover is affixed to the surface and covers the etched grooves. An input line is connected to the filter and an output line is connected to the capillary. A second comb filter can be included in the output line.

6 Claims, 1 Drawing Figure

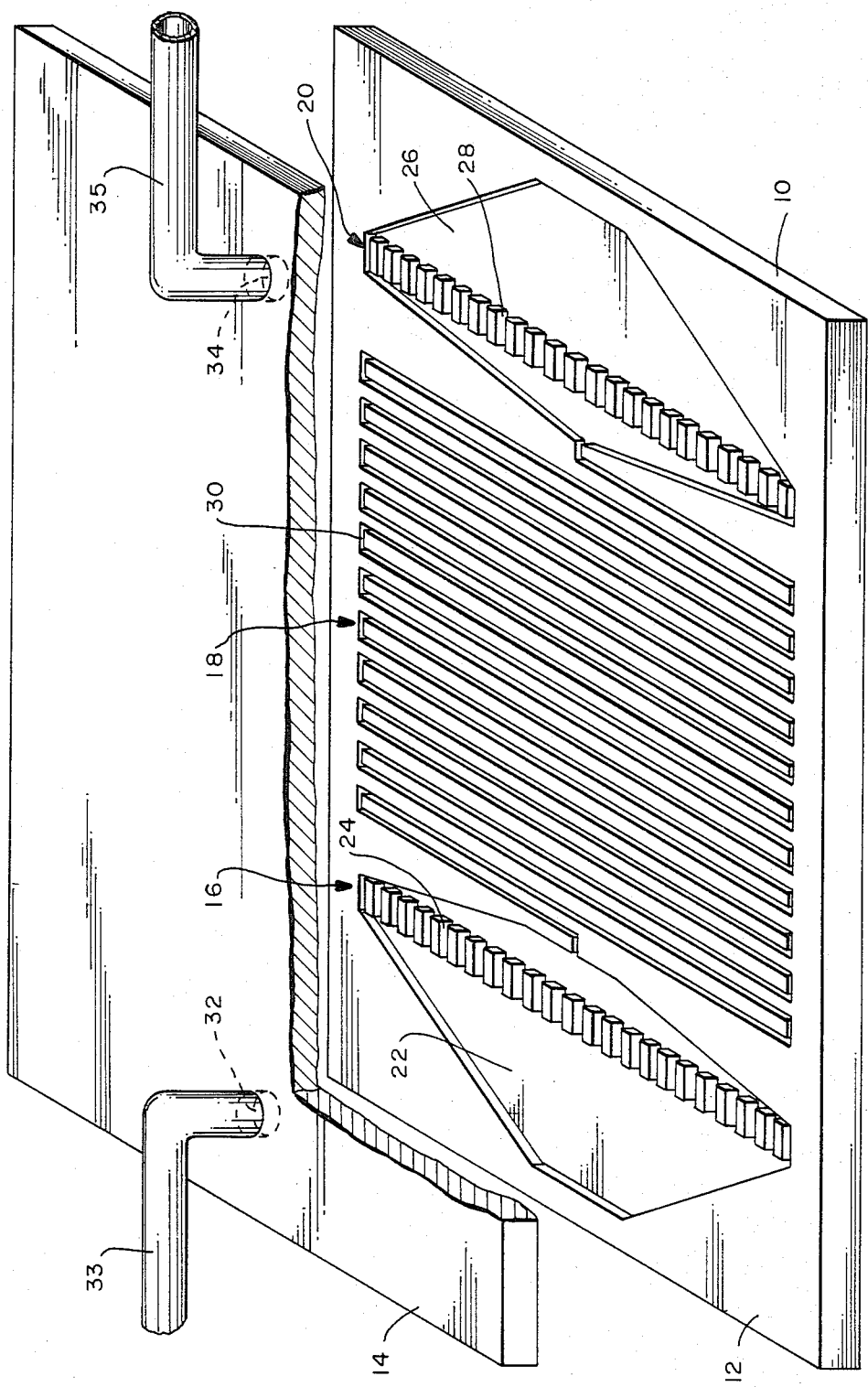

INTEGRAL FLUID FILTER AND CAPILLARY

The U.S. Government has rights in this invention pursuant to National Institute of Health Grant No. NIH-RR-01086.

This invention relates generally to fluid filters, and more particularly the invention relates to an integral fluid filter and capillary.

Capillaries having high resistance to fluid flow are useful in many applications. One such application is as a flow regulator in implantable drug delivery systems.

A problem with any capillary is a tendency to clog when small particles are in the fluid flow channel. Typically, a filter is placed in the fluid delivery line upstream from the capillary. The filter usually consists of a membrane having many pores which are smaller in diameter than the capillary so that particles which could clog the capillary are trapped at the filter. The flow resistance of the filter is designed to be smaller than the flow resistance of the capillary so that the flow resistance of the overall system does not greatly increase as particles are trapped in the filter.

The combined filter and capillary are more expensive than either component alone, the assembling the two components adds significantly to the costs of fabrication. In addition, dirt may enter the capillary before or during the assembly process and clog the capillary.

The present invention is directed to an integral fluid and filter capillary which can be mass produced. Batch fabricated silicon capillaries are known for use in gas chromatography systems. The present invention combines filter means with a capillary in a substrate such as a semiconductor substrate which permits small clog-free capillaries to be more reliably and uniformly produced.

More particularly, the filter membrane heretofore used is replaced by a comb filter comprising many small capillaries in parallel which are placed upstream from the main capillary. The filter and capillary are fabricated as grooves in a surface of a monolithic body such as a semiconductor substrate, for example, using conventional semiconductor processing techniques. The cross sectional dimensions of each capillary within the comb filter are made smaller than the cross sectional dimensions of the main capillary so that the filter catches any particles which could clog the main capillary. A plate of suitable material is attached to the surface of the semiconductor body to form the grooves into closed tubes and complete the filter and capillary structure. A second filter downstream from the main capillary can be included in the integral structure.

Accordingly, an object of the present invention is an integral fluid filter and capillary structure.

Another object of the invention is a fluid filter and capillary which can be batch fabricated.

A feature of the invention is a comb filter having a plurality of parallel capillaries.

Another feature of the invention is a substrate having a major surface in which the filter and capillary structure is formed.

The invention and objects and features thereof will be more readily apparent from the following detailed description and appended claims when taken with the drawing, in which the FIGURE is an exploded perspective view of an integral fluid filter and capillary in accordance with one embodiment of the invention.

Referring now to the drawing, the structure includes a semiconductor substrate 10 having a major surface 12 and a cover 14 for the surface. In a preferred embodiment the semiconductor substrate 10 comprises monocrystalline silicon and the cover 14 comprises a plate of glass.

Formed in the surface 12 of the substrate 10 is a first comb filter shown generally at 16, a main capillary shown generally at 18, and a second comb filter shown generally at 20. The first comb filter 16 is formed adjacent to a recessed portion 22 in the surface 12 with a plurality of parallel capillaries being defined by means of grooves 24. Similarly, the second filter 20 is formed adjacent to a recessed portion 26 in the surface 12 with the parallel capillaries being defined by a plurality of grooves 28. Interconnecting the recess 22 and the recess 26 is a groove 30 which preferably has a larger cross sectional area than the grooves 24 and 28. Groove 30 defines the main capillary.

Access holes 32 and 34 are formed through plate 14 to access the recessed portions 22 and 26, respectively. Hole 32 receives an input line 33 and hole 34 receives an output line 35, with the capillaries 24 functioning as a comb filter upstream from the main capillary 30 and the capillaries 28 functioning as a comb filter downstream from the main capillary 30. It will be appreciated that the downstream filter is not essential to the invention but is included in a preferred embodiment. Plate 14 is bonded to the surface 12 to cover the recessed regions 22 and 26 and the capillaries 24, 28, and 30.

Conventional semiconductor fabrication techniques are employed in forming the recessed regions and grooves. For example, a layer of silicon oxide can be grown on the surface of a monocrystalline silicon substrate. Using a standard photolithography and etching process, a mask pattern for the capillary and comb filters is transferred to the silicon dioxide layer with the oxide in the mask pattern being removed. Thereafter, using the remaining oxide on the surface as a mask, the grooves of the comb filters and the groove for the main capillary are etched in the surface. Preferential etchants such as a solution of potassium hydroxide can be used in the etching process to define the grooves and recessed areas. Alternatively, isotropic etchants such as mixtures of hydroflouric acid and nitric acid may be used. Both methods are well known in the semiconductor processing art.

Thereafter, the remaining oxide is removed from the silicon surface by a suitable etchant, and the glass plate 14 is bonded to the surface using a conventional anodic bonding process, thereby covering the etched recessed portions and grooves.

The holes 32 and 34 are formed in the glass cover 14 by a suitable technique such as ultrasonic drilling, and the input line 33 and output line 35 are affixed to the holes 32, 34 by a suitable sealant or fitting.

An integral fluid filter and capillary in accordance with the invention is readily batch fabricated thereby reducing the cost of the structure, and known techniques for fabricating the structure in silicon permit accurate reproduction. While the invention has been described with reference to a specific embodiment, the description is illustrative of the invention and is not to be construed as limiting the invention. For example, the cover can be a semiconductor or metal body instead of an insulator as above, and the access holes to the recessed portions can be formed through the semiconductor substrate or from the edge of the substrate. For example, the filter grooves can extend to the edge of the substrate and define the fluid input and the fluid output. Other modifications and applications may occur to those skilled in the art without departing from the true spirit and scope of the invention as defined by the appended claims.

What is claimed is:

1. An integral filter and capillary comprising
   a substrate having a major surface,
   a first recessed region on said surface and in said substrate including a first plurality of generally parallel grooves,
   a second groove on said surface and in said substrate connected with said first recessed region adjacent to one end of said first plurality of grooves, said second groove having cross-sectional dimensions greater than the cross-sectional dimensions of said first plurality of grooves,
   a cover affixed to said major surface and covering said first recessed region and said second groove,
   a fluid input to said first recessed region adjacent to one end of said first plurality of grooves opposite from said second groove, and
   a fluid output connected to said second groove.

2. The integral filter and capillary as defined by claim 1 wherein said substrate comprises a semiconductor body and said cover comprises a glass plate.

3. The integral filter and capillary as defined by claim 2 wherein said fluid input includes a first hole through said plate in communication with said first recessed region.

4. The integral filter and capillary as defined by claim 3 wherein said fluid output includes a second recessed region on said surface and in said substrate including a second plurality of generally parallel grooves, said second groove being connected to said second recessed region adjacent to one end of said second plurality of grooves, said cross-sectional dimensions of said second groove being greater than the cross-sectional dimensions of said second plurality of grooves.

5. The integral filter and capillary as defined by claim 4 wherein said fluid output further includes a second hole through said plate in communication with said second recessed region.

6. The integral filter and capillary as defined by claim 1 wherein said fluid output includes a second recessed region on said surface and in said substrate including a second plurality of generally parallel grooves, said second groove being connected to said second recessed region at one end of said second plurality of grooves, said cross-sectional dimensions of said second groove being greater than the cross-sectional dimensions of said second plurality of grooves.

* * * * *